(12) United States Patent
Lai et al.

(10) Patent No.: US 9,730,907 B2
(45) Date of Patent: Aug. 15, 2017

(54) MICROENCAPSULATED OMEGA-3 OIL POWDER FOR ANIMAL FEED

(71) Applicant: SINGAO (XIAMEN) AGRIBUSINESS DEVELOPMENT CO., LTD., Xiamen (CN)

(72) Inventors: Zhouwen Lai, Xiamen (CN); Liang Zhang, Xiamen (CN)

(73) Assignee: Singao (Xiamen) Agribusiness Development Co., Ltd., Xiamen, Fujian (CN)

( * ) Notice: Subject to any disclaimer, the term of this patent is extended or adjusted under 35 U.S.C. 154(b) by 230 days.

(21) Appl. No.: 14/608,206

(22) Filed: Jan. 29, 2015

(65) Prior Publication Data

US 2016/0220521 A1    Aug. 4, 2016

(51) Int. Cl.
| | |
|---|---|
| *A23K 20/158* | (2016.01) |
| *A61K 31/202* | (2006.01) |
| *A61K 9/00* | (2006.01) |
| *A61K 9/50* | (2006.01) |
| *A23L 33/12* | (2016.01) |
| *A23D 9/02* | (2006.01) |
| *A23D 9/06* | (2006.01) |

(52) U.S. Cl.
CPC .............. *A61K 31/202* (2013.01); *A23D 9/02* (2013.01); *A23D 9/06* (2013.01); *A23L 33/12* (2016.08); *A61K 9/0056* (2013.01); *A61K 9/0095* (2013.01); *A61K 9/5036* (2013.01); *A61K 9/5089* (2013.01); *A23V 2002/00* (2013.01)

(58) Field of Classification Search
CPC ...... A23K 20/158; A23K 40/10; A23K 50/30; A23K 50/75; A61K 9/50; A61K 9/5036; A61K 9/5089; B01J 13/02; B01J 13/04
USPC .............................................. 426/2, 98, 471
See application file for complete search history.

(56) References Cited

U.S. PATENT DOCUMENTS

2003/0165572 A1* 9/2003 Auriou ................. A61K 9/1075
                                                                424/493
2009/0196950 A1* 8/2009 Hartnell ................. A23K 1/164
                                                                426/2

FOREIGN PATENT DOCUMENTS

CN           1883294 A  * 12/2006
CN        103044557 A  *  4/2013

* cited by examiner

*Primary Examiner* — Walter Moore
(74) *Attorney, Agent, or Firm* — Seed IP Law Group LLP

(57) ABSTRACT

Disclosed are a microcapsule fat powder of Ω3-enriched meat, egg and milk and its preparation method, and the powder includes a water-soluble wall material and an Ω3 oil core material embedded in the wall material. The water-soluble wall material is prepared by mixing dextrin, water-soluble syrup, whey powder or chitosan with starch paste, and the Ω3 oil core material is prepared by mixing linseed oil, deep sea fish oil or algae oil with a composite emulsifier which is stearic acyl lactylate. The microcapsule fat powder can be combined with intestinal and pancreatic lipases very easily to improve the digestion, absorption and utilization of Ω3 oils.

2 Claims, No Drawings

MICROENCAPSULATED OMEGA-3 OIL POWDER FOR ANIMAL FEED

BACKGROUND OF THE INVENTION (a) Technical Field of the Invention

The present invention relates to a microcapsule fat powder of omega-3 (Ω3) enriched meat, egg and milk, and a preparation method thereof.

(b) Description of the Prior Art

Polyunsaturated fatty acid (PUFA) refers to a linear-chain fatty acid containing two or more double bonds, and the carbon-carbon bond length is equal to the length of 18~22 carbon atoms. PUFA is the main body and core on the research and development of functional fatty acids. Ω3 polyunsaturated fatty acids include α-linolenic acid, EPA and DHA. The α-linolenic acid is a precursor of EPA and DHA and has an effectiveness of over 60% on reducing triglyceride, cholesterol, and β-lipoprotein. EPA is called "Vascular Scavenger" and has the effect of dredging and cleaning up heart blood vessels to prevent various different cardiovascular diseases. DHA (Docosahexaenoic Acid or commonly known as "Gold for brain" is a very important polyunsaturated fatty acid to human body and a very important member of the Ω3 unsaturated fatty acid family. DHA is an important fatty acid ingredient in nerve and visual cells and has important effects for maximizing the normal physiological functions of human body and preventing and treating many diseases, and particularly plays an important role in the development of infant brain and visual system. Human brain contains more than 14 billion neurons, and a large quantity of DHA is existed in brain cells and cell synapses and DHA is a main constituent of human brain cells, and 10% of cell lipids in a human brain is DHA which is a necessary substance for the formation of human brain and the development of intellectual quotient (IQ). Lack of DHA may trigger a series of symptoms including growth retardation, scaly skin, infertility, mental retardation, etc. The intake of Ω3 polyunsaturated fatty acid and the incidence of coronary heart disease are negatively correlated, and DHA and EPA have a better anticancer effect.

The Ω3 polyunsaturated fatty acid occupies 32.9% of fats in sperms and has a significant effect on the mobility and integrity of cell membranes. A large amount of EPA and DHA exists in deep sea fish oils, and the content of Ω3 polyunsaturated fatty acids of salmon, trout, sardine, and tuna oils is not less than 20%.

Linseed oil (or sesame oil) contains 51.7-57% of linolenic acid (ALA or octadecatrienoic acid) which is the main raw material for producing Ω3 enriched eggs. Besides the linseed oil, Ω3 enriched plant seeds (or oils and cakes) such as Sichuan pepper, *carthamus tinctorius*, pine needle, evening primrose, camellia, *perilla frutescens*, Chia, rubber, etc, and even *pennisetum americanum* has a rich content. The production of Ω3 enriched eggs by adding these plant compositions is a result from the effect of ALA. *Schizochytrium* sp. and *Thaustochytrium* sp. are fermented, separated and dried to prepare a feed material with the DHA content over 20%. This technology has matured, and its extensive usage in the feed industry still waits for a significant drop of the production cost.

In today's needs for food, most Chinese people have insufficient intake of Ω3 polyunsaturated fatty acids and just take 80 mg/day which is much lower than the intake of 200 mg/day recommended by American standards, and further lower than the intake of 450 mg/day recommended by European standards. How to increase the content of Ω3 polyunsaturated fatty acids in the structure of our diets has attracted widespread attention, so that the development of food (such as meat, egg and milk) of Ω3 enriched polyunsaturated fatty acids becomes necessary.

Ω3 polyunsaturated fatty acids can be enriched into meat, egg and milk through feeds:

(1) Tie Qi Li Shi Group Ltd. (Sichuan, China) mainly adds 1% of smashed linseeds into the feeds, and this method features the advantages of simple process and low cost and the disadvantage of having two kinds of poisons (VB anti-factor and toxic cyanogenic glycoside included in the linseed) that limit the direct addition of the linseed into the feeds.

(2) Jinjiang Green Health Eggs Co., Ltd (Fujian, China) adds 6% of fish oils, algae powder and linseed to increase the yolk DHA up to 5~6 times, and its core still has an effect of 1.7% of fish oils.

(3) Shanghai Zhanwang Group, Ltd. (Shanghai, China) adds a mixture of linseed oil and deep sea fish oil into fermented feeds containing lactobacillus and feeds laying hens to produce Ω3 enriched eggs.

However, Ω3 polyunsaturated fatty acid may be spoiled and oxidized easily, and the present Ω3 polyunsaturated fatty acids added into the feeds are difficult to be absorbed by poultry or entered into the meat, egg and milk of poultry and livestock.

SUMMARY OF THE INVENTION

In view of the aforementioned problems of the prior art, it is a primary objective of the present invention to overcome the problems by providing a microcapsule fat powder of Ω3-enriched meat, egg and milk, which can be combined with intestinal and pancreatic lipases easily to improve the digestion absorption and utilization of the Ω3 oils, and whose characteristics including anti-oxidation, easy storage, and resistance to spoilage guarantee the content of Ω3 polyunsaturated fatty acids.

To overcome one of the technical problems of the prior art, the present invention provides a microcapsule fat powder of Ω3-enriched meat, egg and milk, the microcapsule fat powder includes a plurality of microcapsule granules, each having a water-soluble wall material and an Ω3 oil core material embedded in the wall material.

Further, the water-soluble wall material is prepared by mixing at least one material selected from the group consisting of dextrin, water-soluble syrup, whey powder and chitosan with starch paste, and the Ω3 oil core material is prepared by mixing at least one oil selected from the group consisting of linseed oil, algae oil and deep sea fish oil with a composite emulsifier and stearic acyl lactylate.

To overcome another technical problem of the prior art, the present invention provides a preparation method of a microcapsule fat powder of Ω3-enriched meat, egg and milk, and products prepared by this method can be combined with intestinal and pancreatic lipases easily to improve the digestion, absorption and utilization of the Ω3 oils, and whose characteristics including anti-oxidation, easy storage, and resistance to spoilage guarantee the content of Ω3 polyunsaturated fatty acids.

The present invention achieves the aforementioned objectives by providing a microcapsule fat powder of Ω3-enriched meat, egg and milk and its preparation method, and the method comprises the following steps:

Step 10: Mix starch with water to form a starch paste. Stir and heat the starch paste to 30~35° C. Add sodium hydroxide into the starch paste until the pH value is 8.5~9. Continue the stirring and activation. Gradually add starch sodium octenylsuccinate diluted by ethanol within 1~2 hours while maintaining and controlling the pH value of the reaction system within a range of 8.2~8.8 during the adding process. Continue the stirring and reaction after the addition of starch sodium octenylsuccinate is completed until the pH value is stabilized at 8.5. Add dilute nitric acid to neutralize the reaction system to a pH of 6.5, and heating up to 90° C. to form the starch paste.

Step 20: Put an Ω3 oil into an oil phase tank. Heat it up to 70~80° C. Put in a composite emulsifier and stearic acyl lactylate while stirring. Maintain the temperature within a range of 70-80° C. and stir until the composite emulsifier and stearic acyl lactylate are dissolved to form an oil phase solution.

Step 30: Put water into an aqueous phase tank. Put in at least one material selected from the group consisting of dextrin, water-soluble syrup, whey powder and chitosan, and disodium hydrogen phosphate, and sodium citrate while stirring. Heat to a temperature of 70~80° C. Add the starch paste prepared in Step 10. Maintain the temperature within a range of 70~80° C. Stir until the starch paste is dissolved to form an aqueous solution.

Step 40: Mix the aqueous solution with the oil phase solution to form a feed solution. Homogenize the feed solution by a high pressure controlled at 20~45 MPa after milling the feed solution by a colloid mill or shearing the feed solution by a shear pump, pressuring to 2~12 MPa. Control an inlet air temperature of a drying tower at 135~190° C. and an outlet air temperature at 55~95° C. to perform a pressure-spray drying process of the feed solution to obtain the microcapsule fat powder of Ω3-enriched meat, egg and milk. Further, the Ω3 oil is one selected from the group consisting of linseed oil, algae oil and deep sea fish oil.

The present invention has the following advantages:

1. Good water solubility: The wall material of the products of the present invention is water soluble, and the emulsified oil core material is suspendable in an aqueous environment. When entering into an aqueous intestinal environment of animals, the products of the present invention are combined with intestinal and pancreatic lipases easily to improve the digestion, absorption and utilization of the Ω3 oils.

2. Anti-oxidation: Materials such as fish oils with high unsaturation and price may be oxidized and spoiled easily, particularly in summer time, and such materials are difficult to produce, store and use. On the other hand, the products of the present invention overcomes the aforementioned problem by special formulation and technology, wherein the Ω3 oil is used as a core material, and water-soluble syrup, whey powder, or chitosan is used as a wall material, and the coated water-soluble wall material isolates the core material from the contact of oxygen, so that the Ω3 fatty acids will not be spoiled or oxidized easily, and its potency is protected to extend the shelf life of oil products and final products significantly and reduce the burden of requiring the very strict conditions for the production, storage and usage of these materials and products, so as to achieve the effect of lowering the Ω3 content of the feed products due to the oxidation and spoilage of oils.

3. Good spreadability: The products of the present invention can be manufactured into microcapsule granule groups of 80-120 meshes which are substantially equal to the particle size of most feed materials, so as to improve the mixing uniformity of the feeds and avoid negative benefits such as agglomeration, non-uniformity, and fermentation and spoilage of residues caused by adding the oil directly. In the meantime, the present invention improves the inconvenience caused by adding oil by feed factories or cultivators, so that users may directly, precisely and conveniently add feeds packaged in a bag into feeds.

DETAILED DESCRIPTION OF THE PREFERRED EMBODIMENTS

The technical content of the present invention will become apparent with the detailed description of preferred embodiments and the illustration of related drawings as follows.

The present invention relates to a microcapsule fat powder of Ω3-enriched meat, egg and milk, and the microcapsule fat powder includes a plurality of microcapsule granules, each having a water-soluble wall material and an Ω3 oil core material embedded in the wall material.

The water-soluble wall material is prepared by mixing at least one material selected from the group consisting of dextrin, water-soluble syrup, whey powder and chitosan with starch paste, and the Ω3 oil core material is prepared by mixing at least one oil selected from the group consisting of linseed oil, algae oil and deep sea fish oil with a composite emulsifier and stearic acyl lactylate.

The mass ratio of the linseed oil or the algae oil to the deep sea fish oil is 0%~100%:100%~0%.

The present invention further relates to a preparation method of the aforementioned microcapsule fat powder of Ω3-enriched meat, egg and milk, and the method comprises the following steps:

Step 10: Mix starch with water to form a starch paste. Stir and heat the starch paste to 30~35° C. Add sodium hydroxide into the starch paste until the pH value is 8.5~9. Continue the stirring and activation. Gradually add starch sodium octenylsuccinate diluted by ethanol within 1~2 hours while maintaining and controlling the pH value of the reaction system within a range of 8.2~8.8 during the adding process. Continue the stirring and reaction after the addition of starch sodium octenylsuccinate is completed until the pH value is stabilized at 8.5. Add dilute nitric acid to neutralize the reaction system to a pH of 6.5, and heating up to 90° C. to form the starch paste.

Step 20: Put an Ω3 oil into an oil phase tank. Heat it up to 70~80° C. Put in a composite emulsifier and stearic acyl lactylate while stirring. Maintain the temperature within a range of 70-80° C. and stir until the composite emulsifier and stearic acyl lactylate are dissolved to form an oil phase solution Step 30: Put water into an aqueous phase tank. Put in at least one material selected from the group consisting of dextrin, water-soluble syrup, whey powder and chitosan, and disodium hydrogen phosphate, and sodium citrate while stirring. Heat the materials to a temperature of 70~80° C. Add the starch paste prepared in Step 10. Maintain the temperature within a range of 70~80° C. Stir until the starch paste is dissolved to form an aqueous solution.

Step 40: Mix the aqueous solution with the oil phase solution to form a feed solution. Homogenize the feed solution by a high pressure controlled at 20~45 MPa after milling the feed solution by a colloid mill or shearing the feed solution by a shear pump, pressuring to 2~12 MPa. Control an inlet air temperature of a drying tower at 135~190° C. and an outlet air temperature at 55~95° C. to perform a pressure-spray drying process of the feed solution to obtain the microcapsule fat powder of Ω3-enriched meat, egg and milk.

The present invention is illustrated by the following preferred embodiments:

Preferred Embodiment 1

An Ω3 enriched microcapsule fat powder is prepared by the method as described below:

Step 10: Add 20 kg of corn starch into 30 kg of drinking water to form a starch paste. Stir and heat the corn starch paste to 30-35° C. Add sodium hydroxide solution (4%) until the pH value is 8.5~9. Continue the stirring and activation for half an hour. Gradually add 0.6 kg of sodium octenyl-succinate anhydride (diluted by 2.4 kg of absolute ethanol or 95% ethanol) within 1~2 hours. As the pH value drops, add sodium hydroxide solution (4%) and maintain the reaction system at pH=8.2~8.8. Continue the stirring and reaction until the pH value is stabilized at 8.5 after sodium octenyl-succinate anhydride has been added. Add dilute hydrochloric acid (3%) to neutralize the reaction system to pH=6.5. Heat up the reaction system to 90° C. to form the starch paste.

Step 20: Put 500 kg of the Ω3 oil into an oil phase tank. Heat it up to 70~80° C. Put in 13 kg of a composite emulsifier and 5.5 kg of stearic acyl lactylate while stirring. Maintain the temperature within a range of 70-80° C. and stir until the composite emulsifier and stearic acyl lactylate are dissolved to form an oil phase solution.

Step 30: Put 950 kg of water into an aqueous phase tank. Put in 470 kg of at least one material selected from the group consisting of dextrin, water-soluble syrup, whey powder and chitosan, and 6 kg of disodium hydrogen phosphate, and 6 kg of sodium citrate while stirring. Heat to a temperature of 70~80° C. Add the starch paste prepared in Step 10. Maintain the temperature within a range of 70~80° C. Stir until the starch paste is dissolved to form an aqueous solution.

Step 40: Mix the aqueous solution with the oil phase solution to form a feed solution, and stir the solution for 20 minutes. Homogenize the feed solution by a high pressure controlled at 20~45 MPa after milling the feed solution by a colloid mill or shearing the feed solution by a shear pump, pressuring to 2~12 MPa. Control an inlet air temperature of a drying tower at 135~190° C. and an outlet air temperature at 55~95° C. to perform a pressure-spray drying process of the feed solution to obtain the microcapsule fat powder of Ω3-enriched meat, egg and milk.

Preferred Embodiment 2

The feed of the Ω3 enriched microcapsule fat powder of the present invention enhances the egg yolk DHA.

Group Division of Experiment:
A: Control Group (BD: Feeds for laying hens supplied by Longyan Company, Hualong Group, Fujian)
B: Experimental Group I (BD+0.5% Fat Hormone)
C: Experimental Group II (BD+1% Fat Hormone)

Each group includes five Hy-line laying hens of 70 weeks age and fed continuously for two weeks, and the results are listed in Table 1:

TABLE 1

|  | A | B | C |
|---|---|---|---|
| Average Egg Weight (g) in Full Course | 66.8 | 65.3 | 72.7 |
| 100 g Yolk C22:6n3 Content (g) | 0.177 | 0.234 | 0.282 |
| Increase Percentage (%) | — | 32.2 | 59.3 |

The results show that:
(1) An addition of 1% of the enriched Ω3 microcapsule fat powder in the daily feeds increases the egg weight by 8.8%.
(2) An addition of 0.5% and 1.0% of the enriched Ω3 microcapsule fat powder in the daily feeds increases the yolk DHA (or C22:6n3) by 32.2% and 59.3% respectively.

Preferred Embodiment 3

The feed by enriched Ω3 microcapsule fat powder of the present invention enriches the DHA better than the feed by enriched liquid oil.

Group Division of Experiment:
A: Control Group (BD: Feeds for laying hens supplied by Longyan Company, Hualong Group, Fujian+1.0% Corn Syrup)
B: Experimental Group I (BD+0.5% Liquid Mixed Oil+0.5% Corn Syrup)
C: Experimental Group II (BD+1% Fat Hormone)

Each group includes five Hy-line laying hens of 80 weeks age and fed continuously for two weeks, and the results are listed in Table 2:

TABLE 2

|  | A | B | C |
|---|---|---|---|
| Average Egg Weight (g) in Full Course | 68.6 | 72.5 | 72.9 |
| 100 g Yolk C22:6n3 Content (g) | 0.170 | 0.220 | 0.292 |
| Increase Percentage (%, for A) | — | 29.4 | 71.8 |
| Increase Percentage (%, for B) | — | — | 32.7 |
| 100 g of Chicken Breast C22:6n3 Content (g) | 0.065 | 0.090 | 0.121 |
| Increase Percentage (%, for A) | — | 38.5 | 86.2 |
| Increase Percentage (%, for B) | — | — | 34.4 |

The results show that:
(1) An addition of 1% of the enriched Ω3 microcapsule fat powder in the daily feeds increases the egg weight by 6.3%.
(2) An addition of 1% of the enriched Ω3 microcapsule fat powder in the daily feeds increases the yolk and chicken breast Ω3 by 32.7% and 34.4% than the liquid mixed oil respectively.

In summation of the description above, the products of the present invention has better Ω3 absorption and conversion rates than other products available in the market, and the aforementioned C22:6n3 is docosahexaenoic acid.

Preferred Embodiment 4

The feed of the Ω3 enriched microcapsule fat powder of the present invention enhances the ALA content and the intramuscular fat content in Huai pork.

Group Division of Experiment:
A: Control Group (BD: Feeds for Huai Pig Farm, Gu Tian, Shanghang County, Longyan City, Fujian)
B: Experimental Group (BD+1% Fat Hormone)

Each group includes 15 Huai pigs with a weight of 120~190 catties and fed continuously for one month, and the results are listed in Table 2:

TABLE 3

|  | A | B |
| --- | --- | --- |
| ALA Content of 100 g in Huai Pork (g) | 0.2571 | 0.5625 |
| Increase Percentage (%) | — | 118.8 |
| Fat Content in 100 g of Huai Pork (g) | 3.911 | 4.205 |
| Increase Percentage (%) | — | 7.52 |

The results show that:
(1) An addition of 2% of the enriched Ω3 microcapsule fat powder in the daily feeds increases the ALA content by 118.8%.
(2) An addition of 2% of the enriched Ω3 microcapsule fat powder in the daily feeds increases the fat content in Huai pork by 7.52%.

When the products of the present invention is under a uniform pressure of 20~45 Mpa, a main structure with a plurality of triglycerides bounded by the bonding forces of molecular bonds is decomposed into a single triglyceride, and the particle size of the oil drops from 20 microns to 2 microns. In the condition of the same particle size, the quantity of emulsified homogeneous single triglycerides is 100,000 times of the quantity of the unprocessed triglycerides. In other words, when the microcapsule wall material is dissolved in the aqueous intestinal environment, single glycerides are formed from disintegration and combined with intestinal lipases and absorbed and used with a chance of 100,000 times more. Animal digestion experiments show that the homogenous emulsified oil has digestion and utilization rates better than those of the unprocessed oil by 15%. The younger the animal, the more significant the difference. If a piglet of 7 weeks age has digestion rates for short and long chained oils equal to 92% and 78% respectively, a piglet of 3 weeks age will have digestion rates for short and long chained oils equal to 90% and 37% respectively.

The present invention has the following advantages:
1. Good water solubility: The wall material of the products of the present invention is water soluble, and the emulsified oil core material is suspendable in an aqueous environment. When entering into an aqueous intestinal environment of animals, the products of the present invention are combined with intestinal and pancreatic lipases easily to improve the digestion, absorption and utilization of the Ω3 oils.
2. Anti-oxidation: Materials such as fish oils with high unsaturation and price may be oxidized and spoiled easily, particularly in summer time, and such materials are difficult to produce, store and use. On the other hand, the products of the present invention overcomes the aforementioned problem by special formulation and technology, wherein the Ω3 oil is used as a core material, and water-soluble syrup, whey powder, or chitosan is used as a wall material, and the coated water-soluble wall material isolates the core material from the contact of oxygen, so that the Ω3 fatty acids will not be spoiled or oxidized easily, and its potency is protected to extend the shelf life of oil products and final products significantly and reduce the burden of requiring the very strict conditions for the production, storage and usage of these materials and products, so as to achieve the effect of lowering the Ω3 content of the feed products due to the oxidation and spoilage of oils.
3. Good spreadability: The products of the present invention can be manufactured into microcapsule granule groups of 80-120 meshes which are substantially equal to the particle size of most feed materials, so as to improve the mixing uniformity of the feeds and avoid negative benefits such as agglomeration, non-uniformity, and fermentation and spoilage of residues caused by adding the oil directly. In the meantime, the present invention improves the inconvenience caused by adding oil by feed factories or cultivators, so that users may directly, precisely and conveniently add feeds packaged in a bag into feeds.

While the invention is described in some detail hereinbelow with reference to certain illustrated embodiments, it is to be understood that there is no intent to limit it to those embodiments. On the contrary, the aim is to cover all modifications, alternatives and equivalents falling within the spirit and scope of the invention as defined by the appended claims.

We claim:
1. A method for preparing a microencapsulated omega-3 (Ω3) polyunsaturated fatty acid (PUFA) powder for Ω3-enriching animal feeds for meat, egg, and milk production, comprising the steps of:
(a) heating to 30-35° C. a starch paste that has been formed by mixing starch and water with continuous stirring and adding sodium hydroxide until the starch paste has a pH value of 8.5-9;
(b) following step (a) with continuous stirring gradually over 1-2 hours adding to the starch paste a composition comprising sodium octenylsuccinate diluted in ethanol while maintaining a pH value of 8.2-8.8 by adding sodium hydroxide until addition of sodium octenylsuccinate is complete and the pH value is stabilized at 8.5;
(c) following step (b) with continuous stirring adding dilute nitric acid to the starch paste until the pH value is 6.5 and then heating the starch paste to 90° C. to obtain a neutralized starch paste;
(d) combining, while stirring and heating to a temperature of 70-80° C. in an aqueous phase tank, water, disodium hydrogen phosphate, sodium citrate, and at least one material selected from the group consisting of dextran, water-soluble syrup, whey powder and chitosan, and then adding to the aqueous phase tank the neutralized starch paste of step (c) until the starch paste is dissolved, to obtain an aqueous solution;
(e) combining, while stirring and heating to a temperature of 70-80° C. in an oil phase tank, an Ω3 oil, stearic acyl lactylate and a composite emulsifier, to obtain an oil phase solution that is maintained at 70-80° C. and in which the stearic acyl lactylate and the composite emulsifier are dissolved;
(f) mixing the aqueous solution of (d) with the oil phase solution of (e) to form a feed solution;
(g) homogenizing the feed solution by a high pressure controlled at 20~45 MPa after milling the feed solution with a colloid mill or shearing the feed solution with a shear pump and pressuring to 2~12 MPa, to obtain a homogenized feed solution; and
(h) pressure spray drying the homogenized feed solution by controlling an inlet air temperature of a drying tower at 135~190° C. and an outlet air temperature of the drying tower at 55~95° C., thereby to obtain the microencapsulated omega-3 (Ω3) polyunsaturated fatty acid (PUFA) powder.
2. The method of claim 1, wherein the Ω3 oil is at least one oil selected from the group consisting of linseed oil, deep sea fish oil, and algae oil.

* * * * *

UNITED STATES PATENT AND TRADEMARK OFFICE
CERTIFICATE OF CORRECTION

Page 1 of 1

PATENT NO. : 9,730,907 B2
APPLICATION NO. : 14/608206
DATED : August 15, 2017
INVENTOR(S) : Zhouwen Lai et al.

It is certified that error appears in the above-identified patent and that said Letters Patent is hereby corrected as shown below:

In the Claims

Column 8, Line 39:
"material selected from the group consisting of dextran" should read --material selected from the group consisting of dextrin--.

Signed and Sealed this
Fifth Day of December, 2017

Joseph Matal
*Performing the Functions and Duties of the*
*Under Secretary of Commerce for Intellectual Property and*
*Director of the United States Patent and Trademark Office*